United States Patent [19]

Roling et al.

[11] Patent Number: 5,693,866

[45] Date of Patent: Dec. 2, 1997

[54] INHIBITORS OF COLOR FORMATION IN ALKANOLAMINES

[75] Inventors: Paul V. Roling, Spring; Quincy K. A. Sintim, Houston; J. Frederick Martin, Conroe, all of Tex.

[73] Assignee: BetzDearborn Inc., Trevose, Pa.

[21] Appl. No.: 635,247

[22] Filed: Apr. 12, 1996

[51] Int. Cl.$^6$ .................................................. C07C 209/90
[52] U.S. Cl. ............................................................ 564/497
[58] Field of Search ................................................ 564/497

[56] References Cited

U.S. PATENT DOCUMENTS 3,819,710  6/1974  Jordan ................................. 260/584 R
4,673,762  6/1987  Paslean et al. ........................... 564/497
5,113,017  5/1992  Smith et al. ................................ 564/2
5,359,139  10/1994 Smith et al. ................................ 564/2

FOREIGN PATENT DOCUMENTS 0004015  9/1979  European Pat. Off. .

Primary Examiner—Brian M. Burn
Attorney, Agent, or Firm—Alexander D. Ricci; Richard A. Paikoff

[57] ABSTRACT

In the thermal processing of crude alkanolamines, a method of inhibiting color formation in the alkanolamines comprising adding an amount, effective for the purpose, of an alkali metal hydroxide or sulfite, or mixtures thereof.

16 Claims, No Drawings

INHIBITORS OF COLOR FORMATION IN ALKANOLAMINES

BACKGROUND OF THE INVENTION

Many decolorizing agents now in use remove color by physical adsorption. The most common materials to remove by this means are represented by charcoals, blacks (such as carbon black), clays and earths. Other compounds remove color by chemical reaction and are frequently more specific as to the materials they can remove color from than the physical adsorption agents. While attempts have been made to predict compound colors, such as by electronegative or steric contributions of substituents to aromatic rings, numerous exceptions to rules relating color to structure require color prediction to be based largely on empirical observations. As a result, attempts to remove color from a specific compound tend to be strictly trial and error operations.

Specific examples may be seen in the decolorization of diethanolamine and triethanolamine. U.S. Pat. Nos. 3,207,790 and 3,159,276 discuss decolorizing ethanolamines with borohydride. Amines may also be decolorized by the use of calcium hydroxide which precipitates contaminant organic salts according to U.S. Pat. Nos. 2,716,136 or with hydrazine in U.S. Pat. No. 2,901,513.

These methods suffer from the high cost and hazard of hydrogen production of the borohydrides, from the need to remove by filtration the calcium precipitates, and the hazard of hydrogen production from the combination of metal and sodium hydroxide.

SUMMARY OF THE INVENTION

The present invention relates to a method of inhibiting color formation in crude alkanolamines by treatment with an alkali metal hydroxide or sulfite, or mixtures thereof.

DESCRIPTION OF THE PREFERRED EMBODIMENTS

During the processing of crude alkanolamines, unacceptable levels of color-bodies are found in the finished products—monoethanolamine (MEA), diethanolamine (DEA) and triethanolamine (TEA). Other examples of alkanolamines include methyldiethanolamine, isopropanolamine, diisopropanolamine and (2-hydroxyethyl)piperazine. It is theorized that the color-bodies are the result of aldehydes, and in particular acetaldehyde, undergoing an aldol condensation reaction.

In testing associated with the present invention, TEA was heated (untreated and treated) at various temperatures for varying periods of time, with the resulting color formation being determined by observing the decrease in percent transmittance on a spectrophotometer at 460 nm. As percent transmittance decreases, color formation increases.

Although many compounds were evaluated, only an alkali metal hydroxide and sulfite (sodium hydroxide and sodium sulfite) were found to more effectively inhibit color formation.

EXAMPLES

Ten mL of TEA and the appropriate amount of treatments (neat or as an aqueous solution when the ppm level was 100 or less) were each added to a test tube. The test tube was then capped with an air atmosphere or argon atmosphere, placed in an oil bath at the appropriate temperature for the stated time, and then removed, cooled, and the percent transmittance determined. Percent transmittance (% T) readings at 460 nm were made in a spectrophotometer. Results are found in Table I.

TABLE I

Percent Transmittance Data for Heat Treated TEA

| Treatment | Temp. (°F.) | ppm (active) | % T at | % T at |
|---|---|---|---|---|
| Set 1 | | | | |
| | | | 3 hours | 23 hours |
| Blank | 330 | — | 72 | 50 |
| NaOH | 330 | 1000 | 84 | 69 |
| Set 2 | | | | |
| | | | 3 hours | 23 hours |
| Blank | 330 | — | 48 | 57 |
| NaOH | 330 | 1000 | 66 | 80 |
| $Na_2SO_3$ | 330 | 5000 | 64 | 92 |
| Set 3 | | | | |
| | | | 48 hours | |
| Blank | 350 | — | 18 | |
| $Na_2SO_3$ | 350 | 5000 | 99 | |
| Set 4 | | | | |
| | | | 48 hours | |
| Blank | 344 | — | 2 | |
| $Na_2SO_3$ | 344 | 5000 | 24 | |
| $Na_2SO_3$ | 344 | 1000 | 70 | |
| $Na_2SO_3$ | 344 | 250 | 78 | |
| NaOH | 344 | 5000 | 70 | |
| NaOH | 344 | 1000 | 56 | |
| NaOH | 344 | 250 | 54 | |
| Set 5 | | | | |
| | | | 64 hours | |
| Blank | 344 | — | 20 | |
| $Na_2SO_3$ | 344 | 5500 | 100 | |
| $Na_2SO_3$ | 344 | 1200 | 98 | |
| $Na_2SO_3$ | 344 | 500 | 94 | |
| Set 6 | | | | |
| | | | 65 hours | |
| Blank | 344 | — | 10 | |
| NaOH | 344 | 250 | 65 | |
| NaOH | 344 | 150 | 45 | |
| NaOH | 344 | 50 | 16 | |
| Set 7 | | | | |
| | | | 65 hours* | |
| Blank | 350 | — | 82 | |
| $Na_2SO_3$ | 350 | 250 | 95 | |
| $Na_2SO_3$ | 350 | 100 | 98 | |
| NaOH | 350 | 250 | 92 | |
| NaOH | 350 | 100 | 87 | |
| $Na_2SO_3$/NaOH | 350 | 125/125 | 100 | |
| $Na_2SO_3$/NaOH | 350 | 50/50 | 95 | |

*Purged tubes for 60 seconds with argon before heating

Sodium hydroxide, sodium sulfite, or combinations of the two surprisingly showed less color formation than the untreated cases whether under air or argon atmosphere. If the aldol condensation reaction of acetaldehyde were occurring, then sodium hydroxide would not have been found effective, because sodium hydroxide is well known to catalyze the aldol condensation reaction.

Comparative Example

TABLE II

Percent Transmittance Data for Heat Treated TEA

| Treatment | Temp. (°F.) | ppm (active) | % T at 3 hours | % T at 23 hours |
|---|---|---|---|---|
| Blank | 330 | — | 72 | 50 |
| $NH_2OH$* | 330 | 5000 | 65 | 11 |

*Aqueous solution of free-base

The preferred embodiments of the present invention, sodium hydroxide or sodium sulfite, can be used neat or in aqueous solutions. Sodium hydroxide or sodium sulfite can be used either alone or in combination. The amount of treatment may range from about 1 to 5000 ppm, with from about 1–1000 ppm preferred. Either treatment may be added after the reactor wherein the alkanolamines are formed, but before the distillation step. Potassium and lithium compounds should function in a similar manner.

While this invention has been described with respect to particular embodiments thereof, it is apparent that numerous other forms and modifications of this invention will be obvious to those skilled in the art. The appended claims and this invention generally should be construed to cover all such obvious forms and modifications which are within the true spirit and scope of the present invention.

We claim:

1. A method of inhibiting color formation in crude alkanolamines comprising adding to said crude alkanolamines an amount, effective for the purpose, of an alkali metal hydroxide.

2. The method as recited in claim 1 wherein said alkali metal hydroxide is sodium hydroxide.

3. The method as recited in claim 1 wherein from about 1–5000 ppm of said alkali metal hydroxide is added to said crude alkanolamines.

4. The method as recited in claim 1 wherein said crude alkanolamines comprise crude monoethanolamine.

5. The method as recited in claim 1 wherein said crude alkanolamines comprise crude diethanolamine.

6. The method as recited in claim 1 wherein said crude alkanolamines comprise crude triethanolamine.

7. The method as recited in claim 3 wherein from about 1–1000 ppm of said alkali metal hydroxide is added to said crude alkanolamines.

8. The method as recited in claim 1 wherein said alkanolamine is selected from the group consisting of methyldiethanolamine, isopropanolamine, diisopropanolamine and (2-hydroxyethyl)piperazine.

9. A method of inhibiting color formation in crude alkanolamines which consists essentially of adding to said crude alkanolamines an amount, effective for the purpose, of an alkali metal hydroxide.

10. The method as recited in claim 9 wherein salad alkali metal hydroxide is sodium hydroxide.

11. The method as recited in claim 9 wherein from about 1–5000 ppm of said alkali metal hydroxide is added to said crude alkanolamines.

12. The method as recited in claim 9 wherein said crude alkanolamines comprise crude monoethanolamine.

13. The method as recited in claim 9 wherein said crude alkanolamines comprise crude diethanolamine.

14. The method as recited in claim 9 wherein said crude alkanolamines comprise crude triethanolamine.

15. The method as recited in claim 9 wherein from about 1–1000 ppm of said alkali metal hydroxide is added to said crude alkanolamines.

16. The method as recited in claim 9 wherein said alkanolamine is selected from the group consisting of methyldiethanolamine, isopropanolamine, diisopropanolamine and (2-hydroxyethyl)piperazine.

* * * * *